US008067337B2

(12) United States Patent
Ikeuchi et al.

(10) Patent No.: US 8,067,337 B2
(45) Date of Patent: Nov. 29, 2011

(54) AGRICULTURAL CHEMICAL COMPOSITION

(75) Inventors: Toshihiro Ikeuchi, Tokyo (JP); Tetsuo Ohkawa, Tokyo (JP); Shuji Ohno, Tokyo (JP); Hiroshi Kawasaki, Tokyo (JP); Ryo Hanai, Tokyo (JP); Yasunori Ogawa, Tokyo (JP); Makoto Fujinami, Tokyo (JP)

(73) Assignee: Kumiai Chemical Industry Co., Ltd, Tokyo (JP)

( * ) Notice: Subject to any disclaimer, the term of this patent is extended or adjusted under 35 U.S.C. 154(b) by 1223 days.

(21) Appl. No.: 11/659,018

(22) PCT Filed: Aug. 5, 2005

(86) PCT No.: PCT/JP2005/014380
§ 371 (c)(1), (2), (4) Date: Jan. 31, 2007

(87) PCT Pub. No.: WO2006/016527
PCT Pub. Date: Feb. 16, 2006

(65) Prior Publication Data
US 2009/0105078 A1 Apr. 23, 2009

(30) Foreign Application Priority Data
Aug. 11, 2004 (JP) ................................. 2004-234798

(51) Int. Cl.
*A01N 25/32* (2006.01)
*A01N 33/00* (2006.01)
*A01N 35/00* (2006.01)
*A01N 37/00* (2006.01)
*A01N 43/00* (2006.01)
*A01N 47/00* (2006.01)
*A01P 13/00* (2006.01)

(52) U.S. Cl. ........ 504/110; 504/189; 504/209; 504/223; 504/235; 504/239; 504/261; 504/291; 504/294; 504/300; 504/320; 504/321; 504/322; 504/323; 504/324; 504/325; 504/326; 504/327; 504/334

(58) Field of Classification Search ........................ None
See application file for complete search history.

(56) References Cited

U.S. PATENT DOCUMENTS

| 5,858,924 | A | * | 1/1999 | Johnson et al. | 504/241 |
| 6,288,088 | B1 | * | 9/2001 | Kando et al. | 514/340 |
| 2004/0224844 | A1 | * | 11/2004 | Bickers et al. | 504/111 |
| 2005/0250648 | A1 | | 11/2005 | Ozaki et al. | |

FOREIGN PATENT DOCUMENTS

| CA | 1 228 244 | | 10/1987 |
| EP | 0 122 231 | | 10/1984 |
| EP | 1 361 218 | | 11/2003 |
| JP | 9-143006 | | 6/1997 |
| JP | 2000-44546 | | 2/2000 |
| JP | 2000-119108 | | 4/2000 |
| JP | 2000-281513 | | 10/2000 |
| WO | WO 0187064 A1 | * | 11/2001 |
| WO | 03/082008 | | 10/2003 |

OTHER PUBLICATIONS

STN online, file CAPLUS, Acc. No. 1959:19364, Doc. No. 53:19364 (Crowdy et al., Annals of Applied Biology (1958), vol. 46, pp. 149-158), Abstract.*
STN online, file CAPLUS, Acc. No. 1950:36689, Doc. No. 44:36689 (Quastel, Advances in Chemistry Series (1950), No. 1, pp. 244-249), Abstract.*

* cited by examiner

*Primary Examiner* — Johann Richter
*Assistant Examiner* — Frank Choi
(74) *Attorney, Agent, or Firm* — Wenderoth, Lind & Ponack, L.L.P.

(57) ABSTRACT

An agricultural chemical composition which enables a wide range of herbicidal compounds including ones showing phytotoxicity to crop plants, etc. upon mere application to exhibit a sufficient herbicidal effect and to show reduced or no phytotoxicity to the crop plants. The agricultural chemical composition comprises (A) a herbicidal compound selected from the group consisting of sulfonylurea compounds, sulfonamide compounds, chloroacetanilide compounds, thiocarbamate compounds, pyrimidinyloxy(thio)benzoic acid compounds, tetrazolinone compounds, pyrazole compounds, cyclohexanedione compounds, phenoxycarboxylic acid compounds, oxazinone compounds, and difluoromethanesulfonylanilide compounds or salts thereof and (B) a compound selected among benzoic acid compounds.

18 Claims, No Drawings

AGRICULTURAL CHEMICAL COMPOSITION

TECHNICAL FIELD

The present invention relates to a pesticide composition and a phytotoxicity reduction method which can reduce or prevent phytotoxicity and reduce the environmental burden.

BACKGROUND ART

It is known that herbicidal compounds in known herbicides such as sulfonylurea compounds, sulfonamide compounds, chloroacetanilide compounds, thiocarbamate compounds, pyrimidinyloxy(thio)benzoic acid compounds, tetrazolinone compounds, pyrazole compounds, cyclohexanedione compounds, phenoxycarboxylic acid compounds, oxazinone compounds, and difluoromethanesulfonylanilide compounds represented by the general formula:

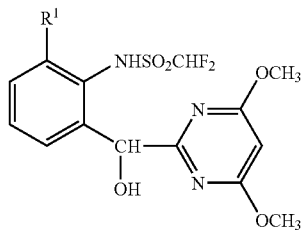

wherein $R^1$ is a hydrogen atom, an alkyl group, or an alkoxyalkyl group, or a salt thereof have high herbicidal effects at low doses on annual weeds such as *Echinochloa crus-galli, Cyperus difformis, Monochoria vaginalis*, and *Ammannia multiflora*, and perennial weeds, such as *Eleocharis acicularis, Sagittaria pygmaea*, and *Sagittaria trifolia* or, in particular, paddy weeds, and have broad herbicidal spectra (see Patent Document 1).

However, these herbicidal compounds may be sometimes phytotoxic to rice, and such phytotoxicity is more severe in a bad environment such as a high temperature environment, sandy soil, or a water-leaking paddy field, and in a shallowly planted seedling or a seedling immediately after transplantation or seeding. Further, these herbicidal compounds may be phytotoxic when applied in excessive amounts unwillingly or accidentally.

Accordingly, more selective herbicidal compounds, or safeners to make herbicidal compounds more selective are now under way of development. Examples of safeners practically used include fenclorim for pretilachlor as a chloroacetanilide compound, and chlorazol for fenoxaprop-ethyl as an allyloxy compound. There has also been proposed an attempt of using a benzoyloxime ether compound as a safener for a sulfonylurea compound (see Patent Document 2). However, these safeners are used only for a particular herbicidal compound, and cannot be widely used.

There has also been proposed an attempt of attaining both of a high herbicidal effect and safety on rice crops by use of a herbicidal compound represented by the above-given general formula in combination with another particular herbicidal compound such as pretilachlor or butachlor (see Patent Document 3). However, a technique of attaining both of a high herbicidal effect and safety on rice crops without using a plurality of herbicide compounds has not been established yet.

Patent Document 1: Japanese Patent Laid-open No. 2000-44546 (claims and elsewhere)
Patent Document 2: European Patent Application No. 122231 (claims and elsewhere)
Patent Document 3: Japanese Patent Laid-open No. 2000-281513 (claims and elsewhere)

DISCLOSURE OF THE INVENTION

In view of such circumstances, an object of the present invention is to provide a pesticide composition that can exhibit a sufficient herbicidal effect and reduce or prevent phytotoxic symptoms, including growth retardation, growth inhibition, tillering inhibition, and etiolation, in an objective crop such as rice, even though a wide variety of herbicidal compounds used therein cause such phytotoxic symptoms in the objective crop when applied alone.

As a result of various studies to develop a pesticide composition having the above-described preferable characteristics, the inventors have found that a pesticide composition containing a conventional herbicidal compound such as a sulfonylurea compound, a sulfonamide compound, a chloroacetanilide compound, a thiocarbamate compound, a pyrimidinyloxy(thio)benzoic acid compound, a tetrazolinone compound, a pyrazole compound, a cyclohexanedione compound, a phenoxycarboxylic acid compound, an oxazinone compound, and a difluoromethanesulfonylanilide compound represented by the general formula (I):

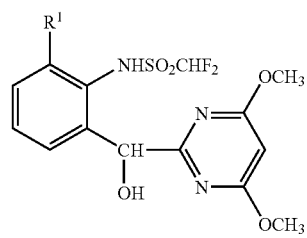

(I)

wherein $R^1$ is a hydrogen atom, an alkyl group, or an alkoxyalkyl group, or a salt thereof, and a specific compound showing no pesticidal activity by itself can contribute to achievement of the object. The present invention has been completed based on this finding.

Namely, the present invention provides a pesticide composition and a phytotoxicity reduction method using the pesticide composition particularly for a gramineous plant as follows:

(1) a pesticide composition characterized by containing (A) a herbicidal compound selected from the group consisting of sulfonylurea compounds, sulfonamide compounds, chloroacetanilide compounds, thiocarbamate compounds, pyrimidinyloxy(thio)benzoic acid compounds, tetrazolinone compounds, pyrazole compounds, cyclohexanedione compounds, phenoxycarboxylic acid compounds, oxazinone compounds, and difluoromethanesulfonylanilide compounds represented by the above-given general formula (I) or a salt thereof, and (B) a compound selected from benzoic acid compounds represented by the general formula (II):

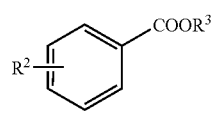

(II)

wherein $R^2$ is a hydrogen atom, an alkyl group having 1 to 15 carbon atoms, a hydroxyl group, a nitro group, or an amino group, and $R^3$ is a hydrogen atom, a metal atom, or an alkyl group;

(2) the pesticide composition according to (1) above, wherein the benzoic acid compound is a compound selected from the group consisting of p-alkylbenzoic acids, p-aminobenzoic acid, p-hydroxybenzoic acid, salts thereof, and esters thereof;
(3) the pesticide composition according to (1) above, wherein the sulfonylurea compound is bensulfuron-methyl, pyrazosulfuron-ethyl, halosulfuron-methyl, azimsulfron, cinosulfuron, cyclosulfamuron, flucetosulfuron, imazosulfuron, or ethoxysulfuron;
(4) the pesticide composition according to (1) above, wherein the sulfonamide compound is penoxsulam;
(5) the pesticide composition according to (1) above, wherein the chloroacetanilide compound is butachlor, pretilachlor, or thenylchlor;
(6) the pesticide composition according to (1) above, wherein the thiocarbamate compound is thiobencarb, esprocarb, or molinate;
(7) the pesticide composition according to (1) above, wherein the pyrimidinyloxy(thio)benzoic acid compound is pyriminobac-methyl, pyriftalid, bispyribac-sodium, or pyribenzoxime;
(8) the pesticide composition according to (1) above, wherein the tetrazolinone compound is fentrazamide;
(9) the pesticide composition according to (1) above, wherein the pyrazole compound is pyrazolate, pyrazoxyfen, or benzofenap;
(10) the pesticide composition according to (1) above, wherein the cyclohexanedione compound is benzobicyclon, mesotrione, or a compound represented by the formula:

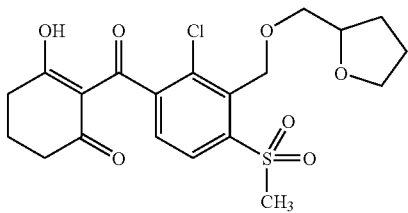

(hereinafter referred to as "AVH-301");
(11) the pesticide composition according to (1) above, wherein the phenoxycarboxylic acid compound is 2,4-D, MCPA, MCPB, or chlomeprop;
(12) the pesticide composition according to (1) above, wherein the oxazinone compound is oxaziclomefone;
(13) the pesticide composition according to (1) to (12) above, further containing a surfactant; and
(14) a method for reducing phytotoxicity by herbicidal compounds which is characterized by applying, simultaneously or in close succession, (A) a herbicidal compound selected from the group consisting of sulfonylurea compounds, sulfonamide compounds, chloroacetanilide compounds, thiocarbamate compounds, pyrimidinyloxy(thio)benzoic acid compounds, tetrazolinone compounds, pyrazole compounds, cyclohexanedione compounds, phenoxycarboxylic acid compounds, oxazinone compounds, and difluoromethanesulfonylanilide compounds represented by the above-given general formula (I) or a salt thereof, and (B) a compound selected from benzoic acid compounds represented by the above-given general formula (II).

Preferable examples of the herbicidal compound as the component (A) in the composition of the present invention include bensulfuron-methyl, pyrazosulfuron-ethyl, halosulfuron-methyl, penoxsulam, azimsulfron, cinosulfuron, cyclosulfamuron, flucetosulfuron, imazosulfuron, ethoxysulfuron, butachlor, pretilachlor, thenylchlor, thiobencarb, esprocarb, molinate, pyriminobac-methyl, pyriftalid, bispyribac-sodium, pyribenzoxime, pyrazolate, pyrazoxyfen, benzofenap, benzobicyclon, mesotrione, AVH-301, 2,4-D, MCPA, MCPB, chlomeprop, oxaziclomefone, fentrazamide, and a difluoromethanesulfonylanilide compound represented by the above-given general formula (I) or a salt thereof.

$R^1$ in the compound represented by the general formula (I) is preferably a hydrogen atom, a linear or branched alkyl group having 1 to 6 carbon atoms, or a linear or branched alkoxyalkyl group having 2 to 6 carbon atoms in total. As the alkyl group, a methyl group, ethyl group, n-propyl group, isopropyl group, isobutyl group, sec-butyl group, t-butyl group, n-pentyl group, 1-methylbutyl group, n-hexyl group, and the like are preferable. As the alkoxyalkyl group, a methoxymethyl group, methoxyethyl group, ethoxyethyl group, 3-ethoxypropyl group, 1-methyl-3-methoxybutyl group, and the like are preferable.

Particularly preferable compounds among the compounds represented by the general formula (I) include, for example, compounds described in Japanese Patent Laid-open No. 2000-44546 such as 2-[(4,6-dimethoxypyrimidin-2-yl)hydroxymethyl]-N-difluoromethanesulfonylanilide, 2-[(4,6-dimethoxypyrimidin-2-yl)hydroxymethyl]-6-methoxymethyl-N-difluoromethanesulfonylanilide, and 2-[(4,6-dimethoxypyrimidin-2-yl)hydroxymethyl]-6-ethyl-N-difluoromethanesulfonylanilide.

Examples of the salt of the herbicidal compound represented by the general formula (I) include a sodium salt and a potassium salt.

Almost all components (A) used in the pesticide composition of the present invention are known compounds described in The Pesticide Manual, 13th edition [published by British Crop Protection Council, 2004], WO 00/21924, and WO 2003/061388.

In the composition of the present invention, the benzoic acid compound as the component (B) used in combination with the herbicidal compound as the component (A) for reducing phytotoxicity thereby is a compound represented by the above-given general formula (II) including, for example, p-alkylbenzoic acids such as p-ethylbenzoic acid, p-(n-propyl)benzoic acid, p-(n-butyl)benzoic acid, p-(t-butyl)benzoic acid, p-(n-pentyl)benzoic acid [hereafter referred to as p-(n-amyl)benzoic acid], and p-(n-hexyl)benzoic acid, p-aminobenzoic acid, p-hydroxybenzoic acid, salts thereof, and alkyl esters thereof.

As the above-mentioned salts, metal salts are preferable, alkali salts are particularly preferable, and sodium salts are more particularly preferable including, for example, sodium p-(t-butyl)benzoate.

Examples of the above-mentioned alkyl esters include methyl p-(t-butyl)benzoate, n-propyl p-hydroxybenzoate, isopropyl p-hydroxybenzoate, n-butyl p-hydroxybenzoate, and isobutyl p-hydroxybenzoate.

In the composition of the present invention, herbicidal compounds other than above may be used in combination.

In the pesticide composition of the present invention, the proportion of use between component (B) and component (A) should, though adequately variable depending on the types of both, types and growing period of the objective crops such as, for example, the transplantation of rice and the like, be such that the mass amount of the component (B) is usually 0.1 to 200 times relative to the mass amount of the component (A). The mass amount of the component (B) is preferably selected in the range of 5 to 100 times relative to a sulfonylurea compound, 20 to 100 times relative to a sulfonamide compound, 0.5 to 10 times relative to a chloroacetanilide compound, 0.25 to 1 time relative to a thiocarbamate compound, 5 to 50 times relative to a pyrimidinyloxy(thio)benzoic acid compound, 3 to 30 times relative to a tetrazolinone compound, 0.25 to 10 times relative to a pyrazole compound, 1 to 50 times relative to a cyclohexanedione compound, 0.25 to 5 times relative to a phenoxycarboxylic acid compound, 10 to 50 times relative to an oxazinone compound, and 0.2 to 100 times or, particularly preferably, 0.5 to 50 times relative to the compound represented by the general formula (I).

In the pesticide composition of the present invention, the amount of the component (A) to be applied is, though not particularly limited, selected, per hectare of an agricultural land, in the range, usually, of 1 to 200 g or preferably, 5 to 100 g as a sulfonylurea compound, 5 to 50 g or, preferably, 10 to 30 g as a sulfonamide compound, 50 to 3,000 g or, preferably, 100 to 2,000 g as a chloroacetanilide compound, 500 to 5,000 g or, preferably, 1,000 to 4,000 g as a thiocarbamate compound, 5 to 500 g or, preferably, 10 to 200 g as a pyrimidinyloxy(thio)benzoic acid compound, 50 to 1,000 g or, preferably, 100 to 500 g as a tetrazolinone compound, 100 to 5,000 g or, preferably, 500 to 3,000 g as a pyrazole compound, 5 to 1,000 g or, preferably, 10 to 500 g as a cyclohexanedione compound, 50 to 2,000 g or, preferably, 100 to 1,000 g as a phenoxycarboxylic acid compound, 5 to 200 g or, preferably, 10 to 100 g as an oxazinone compound, and 5 to 200 g or, preferably, 10 to 100 g as the compound represented by the general formula (I).

In the pesticide composition of the present invention, the amount of the component (B) to be applied is, though not particularly limited, selected, per hectare of an agricultural land, in the range, usually, of 10 to 5,000 g or, preferably, 50 to 3,000 g or, more preferably 100 to 2,000 g.

The pesticide composition of the present invention may contain an additional component usually used in pesticide formulations according to need.

Examples of the additional component include a carrier such as a solid carrier or liquid carrier, a surfactant, a binder, a tackifier, a thickener, a colorant, a spreader, a sticker, an antifreezing agent, an anticaking agent, a disintegrator, and a stabilizer.

In addition, as the additional component, a preservative, a plant detritus, and the like may also be used according to need.

These additional components can be used singly or can be used as a combination of two kinds or more.

The above-mentioned additional components will be described.

Examples of the solid carrier include natural minerals such as quartz, clay, kaolinite, pyrophylite, sericite, talc, bentonite, acid clay, attapulgite, zeolite, and diatomaceous earth; inorganic salts such as calcium carbonate, ammonium sulfate, sodium sulfate, and potassium chloride; organic solid carriers such as synthetic silicic acid, synthetic silicate, starch, cellulose, and a vegetable powder; and plastic carriers such as polyethylene, polypropylene, and poly(vinylidene chloride). These can be used singly or can be used as a combination of two kinds or more.

Examples of the liquid carrier include alcohols including monohydric alcohols such as methanol, ethanol, propanol, isopropanol, and butanol, and polyhydric alcohols such as ethyleneglycol, diethyleneglycol, propyleneglycol, hexyleneglycol, polyethyleneglycol, polypropyleneglycol, and glycerol; polyhydric alcohol compounds such as propylene-based glycol ethers; ketones such as acetone, methyl ethyl ketone, methyl isobutyl ketone, diisobutyl ketone, and cyclohexanone; ethers such as ethyl ether, dioxane, ethyleneglycol monoethyl ether, dipropyl ether, and tetrahydrofuran; aliphatic hydrocarbons such as normal paraffin, naphthene, isoparaffin, kerosine, and mineral oil; aromatic hydrocarbons such as benzene, toluene, xylene, solvent naphtha, and alkylnaphthalene; halogenated hydrocarbons such as dichloroethane, chloroform, and carbon tetrachloride; esters such as ethyl acetate, diisopropyl phthalate, dibutyl phthalate, dioctyl phthalate, and dimethyl adipate; lactones such as γ-butyrolactone; amides such as dimethylformamide, diethylformamide, dimethylacetamide, and N-alkylpyrrolidinone; nitriles such as acetonitrile; sulfur compounds such as dimethyl sulfoxide; vegetable oils such as soybean oil, rapeseed oil, cotton seed oil, and castor oil; and water. These can be used singly or can be used as a combination of two kinds or more.

Examples of the surfactant include nonionic surfactants such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl phenyl ether, polyoxyethylene dialkyl phenyl ether, a polyoxyethylene alkyl phenyl ether-formalin condensate, a polyoxyethylene-polyoxypropylene block polymer, alkylpolyoxyethylene-polypropylene block polymer ether, polyoxyethylenealkylamine, polyoxyethylene fatty acid amide, polyoxyethylene fatty acid bisphenyl ether, polyalkylene benzyl phenyl ether, polyoxyalkylene styryl phenyl ether, acetylene diol, polyoxyalkylene-added acetylene diol, polyoxyethylene ether-type silicone, ester-type silicone, a fluorine surfactant, polyoxyethylene castor oil, and hydrogenated polyoxyethylene castor oil; anionic surfactants such as alkyl sulfate, polyoxyethylene alkyl ether sulfate, polyoxyethylene alkyl phenyl ether sulfate, polyoxyethylene styryl phenyl ether sulfate, alkylbenzenesulfonate, ligninsulfonate, alkylsulfosuccinate, naphthalenesulfonate, alkylnaphthalenesulfonate, a salt of a formalin condensate of naphthalenesulfonic acid, a salt of a formalin condensate of alkylnaphthalenesulfonic acid, fatty acid salt, polycarboxylate, N-methyl-fatty acid sarcosinate, resinate, polyoxyethylene alkyl ether phosphate, and polyoxyethylene alkyl phenyl ether phosphate; cationic surfactants such as laurylamine hydrochloride, stearylamine hydrochloride, oleylamine hydrochloride, stearylamine acetate, stearylaminopropylamine acetate, and alkylamine salts including alkyltrimethylammonium chloride and alkyldimethylbenzalkonium chloride; and ampholytic surfactants such as an amino acid or betaine surfactant.

These surfactants can be used singly or can be used as a combination of two kinds or more.

Examples of the binder and tackifier include carboxymethylcellulose and a salt thereof, dextrin, water-soluble starch, xanthan gum, guar gum, sucrose, poly(vinylpyrrolidone), gum arabic, poly(vinyl alcohol), poly(vinyl acetate), sodium polyacrylate, poly(ethylene glycol) with an average molecular weight of 6,000 to 20,000, polyethylene oxide with an average molecular weight of 100,000 to 5,000,000, and phospholipid (for example, cephalin and lecitin).

Examples of the thickener include water-soluble polymers such as xanthan gum, guar gum, carboxymethylcellulose, poly(vinylpyrrolidone), a carboxyvinyl polymer, an acrylic polymer, a starch compound, and a water-soluble polysaccharide; and inorganic fine powders such as high-purity bentonite and fumed silica (white carbon).

Examples of the colorant include inorganic pigments such as iron oxide, titanium oxide, and Prussian blue; and organic dyes such as an alizarin dye, azo dye, and metal phthalocyanine dye.

Examples of the spreader include a silicone surfactant, a cellulose powder, dextrin, modified starch, a polyaminocarboxylic acid chelate compound, crosslinked polyvinylpyrrolidone, a copolymer of maleic acid with styrene, a (meth) acrylic acid copolymer, a half ester of a polymer composed of polyhydric alcohol with dicarboxylic anhydride, and a water-soluble salt of polystyrenesulfonic acid.

Examples of the sticker include paraffin, terpene, a polyamide resin, polyacrylate, polyoxyethylene, wax, polyvinyl alkyl ether, an alkylphenol-formalin condensate, and a synthetic resin emulsion.

Examples of the antifreezing agent include polyhydric alcohols such as ethylene glycol, diethylene glycol, propylene glycol, and glycerol.

Examples of the anticaking agent include polysaccharides such as starch, alginic acid, mannose, and galactose; poly(vinylpyrrolidone), fumed silica (white carbon), ester gum, and a petroleum resin.

Examples of the disintegrator include sodium tripolyphosphate, sodium hexametaphosphate, metal stearates, a cellulose powder, dextrin, a methacrylate copolymer, polyvinylpyrrolidone, a polyaminocarboxylic acid chelate compound, a sulfonated styrene-isobutylene-maleic anhydride copolymer, and a starch-polyacrylonitrile graft copolymer.

Examples of the stabilizer include desiccants such as zeolite, calcined lime, and magnesium oxide; and ultraviolet absorbers such as a salicylic acid and benzophenone ultraviolet absorber.

Examples of the preservative include potassium sorbate and 1,2-benzthiazolin-3-one.

Examples of the plant detritus include sawdust, coconut shell, corn cob, and tobacco stalk.

When the above-mentioned additional component is contained in the pesticide composition of the present invention, a content thereof is selected in the range of, on a mass basis, usually 5 to 95% or, preferably, 20 to 90% as a carrier, usually 0.1 to 30% or, preferably, 0.5 to 10% as a surfactant, and 0.1 to 30% or, preferably, 0.5 to 10% as other additives.

The pesticide composition of the present invention can be employed as prepared in any desired formulations such as liquid formulations, emulifiable concentrates, wettable powders, dust formulations, oil solutions, water dispersible granules, suspension concentrates, emulsion waters, granules, jumbo formulations, suspo-emulsions, microcapsules and others.

During the formulation, the composition may be prepared as a mixture with a pesticide other than the component (A) including, for example, another herbicide, an insecticide, a fungicide, a plant growth regulator, or a fertilizer.

The pesticide composition of the present invention can be in the form obtained by wrapping any of the above-mentioned formulations with a water-soluble film. Application thereof in this form may contribute to manpower saving and also may improve safety.

The pesticide composition of the present invention can be applied at any time from pre-emergence of weeds to the growing period of weeds so as to concurrently accomplish eradication of weeds and reduce phytotoxicity against the objective crops. The objective crop is preferably rice, because the composition of the present invention is most effective if applied to rice.

In the method of the present invention, it is optional that the above-mentioned component (A) and component (B) are applied simultaneously or applied in close succession.

The "application in close succession" implied here has a meaning that the above-mentioned component (B) is applied with a short interval from application of the above-mentioned component (A) before appearance of any phytotoxicity on the objective crops due to the component (A).

In the simultaneous application, application can be made in a ready-mixed form so that, for example, a ready-prepared composition of the present invention can be used or the above-mentioned component (A) and component (B) are prepared separately to conduct application by blending them just before use as an in-situ blend or, namely, in the form of a tank mix.

The method for producing the pesticide composition of the present invention is not particularly limited but usually includes the following methods:

a method in which a blend of all starting materials is admixed with an appropriate volume of water for kneading followed by extrusion through a screen having an opening of a specified size for granulation, and drying;

a method in which a herbicidal compound, a benzoic acid compound, and a surfactant are dissolved or suspended in an organic solvent so as to cause the solution or suspension to be adsorbed on a carrier; and a method in which a blend of all starting materials are mixed and pulverized with a suitable mill.

BEST MODE FOR CARRYING OUT THE INVENTION

Next, the best mode for carrying out the present invention will be described with reference to Examples. In the following description, "part(s)" refers to "part(s) by mass". "Untreated area" refers to a crop area in which a crop has been grown as in respective Examples using neither the component (A) nor the component (B) of the present invention.

Examples 1 to 13

Brine-sorted rice seeds (variety of Kinmaze) were soaked in a 0.5% aqueous solution of sodium hypochlorite for 10 minutes followed by washing in running water for 30 minutes and then kept at 30° C. for 36 hours to cause germination for obtaining germinated seeds. Separately, 0.3 part of gellan gum was dissolved in 100 parts of an aqueous solution of salts for Hoagland's No. 2 culture medium (a product by Sigma Co.). 13 Glass vials of 2 cm internal diameter and 5 cm height were each filled with 15 ml of the solution to which 2-[(4,6-dimethoxypyrimidin-2-yl)hydroxymethyl]-6-methoxymethyl-N-difluoromethane-sulfonylanilide (hereinafter referred to as the herbicidal compound A1) and a variety of the benzoic acid compounds indicated in Table 1 were added to make up concentrations of 0.15 ppm and 2 ppm, respectively, and kept standing to cause gelation of the solutions in the glass vial to prepare a culture medium containing the inventive composition (hereinafter referred to as the inventive culture medium). Besides, gellan gum alone was dissolved likewise in the same proportion in the above-mentioned aqueous solution of the salts for culture medium and a glass vial filled with 15 ml of the solution was kept standing to obtain a culture medium in which the aqueous solution was gelled in the glass vial (hereinafter referred to as the untreated medium). Onto these culture media, each five grains of the above-mentioned germinated rice seeds were seeded. After seeding, the above-mentioned germinated rice seeds were grown in a growth chamber (manufactured by SANYO Electric Co., Ltd.) under the conditions of the temperature at 25° C. with the lighting period of 16 hours, and the dark period of 8 hours to measure the lengths of the roots after 7 days or, namely, after lapse of 7 cycles. By taking the respective average values for the determined values for the crop division in each of the Examples in which growing was effected in the inventive culture medium and for the crop division in which growing was effected in an untreated culture medium (referred to hereinafter as the untreated division), Table 1 shows the results in percentages of the determined value of each crop division of the Examples relative to the determined value of the untreated area.

Comparative Example 1

Germinated seeds were grown in the same manner as in Example 1, except for not adding a benzoic acid compound to the inventive culture medium. After seven days, the lengths of the roots were measured. By taking the average value for the determined values, Table 1 shows the results in a percentage in the same manner as in the respective Examples.

TABLE 1

| | Benzoic acid compound | Length of root (%) |
|---|---|---|
| Example 1 | p-Ethylbenzoic acid | 25 |
| Example 2 | p-(n-Propyl)benzoic acid | 27 |
| Example 3 | p-(n-Butyl)benzoic acid | 66 |
| Example 4 | p-(n-Amyl)benzoic acid | 70 |
| Example 5 | p-(n-Hexyl)benzoic acid | 43 |
| Example 6 | p-(t-Butyl)benzoic acid | 47 |
| Example 7 | Sodium p-(t-butyl)benzoate | 41 |
| Example 8 | Methyl p-(t-butyl)benzoate | 25 |
| Example 9 | p-Aminobenzoic acid | 37 |
| Example 10 | n-Propyl p-hydroxybenzoate | 37 |
| Example 11 | Isopropyl p-hydroxybenzoate | 31 |
| Example 12 | n-Butyl p-hydroxybenzoate | 44 |
| Example 13 | Isobutyl p-hydroxybenzoate | 44 |
| Comparative Example 1 | — | 21 |
| Untreated area | — | 100 |

Examples 14 to 20

The test culture media were prepared by adding, in advance, to a 25% aqueous solution of salts for Murashige & Skoog culture medium (a product of Wako Pure Chemical Industries, Ltd.), the herbicidal compound A1 and various benzoic acid compounds indicated in Table 2 to make up a concentration of 0.1 ppm and the concentrations shown in Table 2, respectively. Fifty ml each of the resulting test culture media were dispensed into a 50 ml Erlenmeyer flask to prepare various liquid culture media. Similarly, the same amount of the 25% aqueous solution of salts for Murashige & Skoog culture medium was added to the above-mentioned flask to prepare a liquid culture medium (hereinafter referred to as the untreated culture medium). Rice (Kinmaze) grown to the second leaf stage in culture soil for raising seedlings was soaked in these culture media, with the root cut off except for a 2 cm-long part thereof, and was grown in a growth chamber under the conditions of 25° C. with the lighting period of 16 hours, and the dark period of 8 hours to measure the plant length of rice, the length of the root and the living masses of the above-ground part and the root after 14 days or, namely, after lapse of 14 cycles. The determined values are shown in Table 2.

Comparative Example 2

Rice was grown in the same manner as in Example 14, except for not adding a benzoic acid compound. After 14 days, the plant length of rice, the length of the root, and the living masses of the above-ground part and the root were measured. The determined values are shown in Table 2.

TABLE 2

| | Benzoic acid compound | | Plant length (cm) | Length of root (cm) | Living mass | |
|---|---|---|---|---|---|---|
| | Compound name | Concentration (ppm) | | | Above-ground part (g) | Root (g) |
| Example 14 | p-(n-Butyl)benzoic acid | 3 | 25.9 | 5.6 | 0.49 | 0.29 |
| Example 15 | p-(n-Butyl)benzoic acid | 1 | 23.6 | 6.3 | 0.37 | 0.20 |
| Example 16 | p-(n-Amyl)benzoic acid | 3 | 27.6 | 6.2 | 0.52 | 0.39 |
| Example 17 | p-(n-Amyl)benzoic acid | 1 | 25.2 | 6.0 | 0.41 | 0.23 |
| Example 18 | p-(n-Hexyl)benzoic acid | 3 | 24.7 | 3.7 | 0.36 | 0.18 |
| Example 19 | p-(t-Butyl)benzoic acid | 3 | 25.6 | 8.5 | 0.49 | 0.27 |
| Example 20 | p-(t-Butyl)benzoic acid | 1 | 21.7 | 2.9 | 0.31 | 0.18 |
| Comparative Example 2 | — | 0 | 15.6 | 2.1 | 0.16 | 0.07 |
| Untreated area | — | 0 | 27.0 | 7.3 | 0.70 | 0.45 |

Examples 21 to 25

The test media were prepared by adding, in advance, to a 25% aqueous solution of salts for Murashige & Skoog culture medium (a product by Wako Pure Chemical Industries, Ltd.), various herbicidal compounds indicated in Table 3 and p-(t-butyl)benzoic acid to make up concentrations indicated in Table 3 and a concentration of 3 ppm, respectively. Fifty ml each of the resulting test culture media were dispensed into a 50 ml Erlenmeyer flask to prepare various liquid culture media. Similarly, a liquid culture medium with a herbicidal compound and a benzoic acid compound not added was prepared. Rice (Kinmaze) grown to the second leaf stage in culture soil for raising seedlings was soaked in these culture media, with the root cut off except for a 2 cm-long part thereof, and was grown in a growth chamber (manufactured by SANYO Electric Co., Ltd.) under the conditions of 25° C. with the lighting period of 16 hours, and the dark period of 8 hours to measure the plant length of rice, the length of the root, and the living masses of the above-ground part and the root after 14 days. The determined values are shown in Table 3.

Comparative Examples 3 to 7

Rice was grown in the same manner as in each of Examples 21 to 25, except for not adding a benzoic acid compound to the culture medium. After 14 days, the plant length of rice, the length of the root, and the living masses of the above-ground part and the root were measured. The determined values are shown in Table 3.

TABLE 3

| | Concentration of herbicidal compound (ppm) | Plant length (cm) | Length of root (cm) | Living mass Above-ground part (g) | Root (g) |
|---|---|---|---|---|---|
| Example 21 | Bensulfuron-methyl | 22.9 | 8.1 | 0.34 | 0.17 |
| Comparative Example 3 | 0.1 | 12.4 | 2.2 | 0.11 | 0.05 |
| Example 22 | Pyrazosulfuron-ethyl | 12.1 | 2.3 | 0.11 | 0.06 |
| Comparative Example 4 | 0.1 | 11.7 | 2.0 | 0.07 | 0.04 |
| Example 23 | Butachlor | 24.4 | 10.5 | 0.52 | 0.25 |
| Comparative Example 5 | 0.3 | 15.5 | 2.8 | 0.14 | 0.09 |
| Example 24 | Thiobencarb | 21.9 | 10.4 | 0.32 | 0.19 |
| Comparative Example 6 | 3 | 19.4 | 8.1 | 0.23 | 0.18 |
| Example 25 | Fentrazamide | 14.2 | 6.3 | 0.21 | 0.11 |
| Comparative Example 7 | 0.1 | 11.6 | 2.2 | 0.08 | 0.05 |
| Untreated area | — | 25.5 | 7.0 | 0.38 | 0.26 |

As is clear from Table 1, Table 2, and Table 3, the compositions of respective Examples in which a benzoic acid compound was added were superior to the compositions of Comparative Examples in which only a herbicidal compound was used, in terms of the plant length, the length of the root, and the living masses of the above-ground part and the root. This shows that the pesticide composition of the present invention is obviously advantageous compared with those of Comparative Examples.

Example 26

A 1/5,000 a Wagner pot was filled with paddy soil (sand soil). After watering and scraping, the water depth was kept at 4 cm. On the following day, rice (Kinmaze) grown to the second leaf stage in culture soil for raising seedlings was prepared with the root cut off except for a 0.5 cm-long part thereof, and each stock of rice was transplanted so that the base had a depth of 2 cm. Three days after the transplantation, granules containing a herbicidal compound A1 in 0.7% and a wettable powder containing p-(t-butyl)benzoic acid in 10% were uniformly sprayed over the water surface of the Wagner pot in equivalents of 10 g ai/10 a and 150 g ai/10 a, respectively. The water loss in depth in 10 days from the day of the chemical treatment was 1 cm/day and 10 cm in total. 45 Days after the chemical treatment, the plant length and the number of tiller stems were measured. The determined values are shown in Table 4.

Comparative Example 8

Rice was grown in the same manner as in Example 26, except for not spraying a benzoic acid compound over the pot. After 45 days, the plant length and the number of tiller stems were measured. The determined values are shown in Table 4.

TABLE 4

| | Plant length (% ratio relative to that of untreated area) | Number of tiller stems |
|---|---|---|
| Example 26 | 100 | 8.5 |
| Comparative Example 8 | 91 | 4.5 |
| Untreated area | 100 | 7.8 |

Examples 27 to 38

A 1/5,000 a Wagner pot was filled with paddy soil (sand soil). After watering and scraping, the water depth was kept at 4 cm. On the following day, rice (Kinmaze) grown to the second leaf stage in culture soil for raising seedlings was prepared with the root cut off except for a 0.5 cm-long part thereof, and each stock of rice was transplanted so that the base had a depth of 2 cm. On the following day of the transplantation, a wettable powder containing various herbicidal compounds indicated in Table 1 in 10% and a wettable powder containing p-(t-butyl)benzoic acid in 10% were uniformly sprayed over the water surface of the Wagner pot in a test dose equivalent indicated in Table 5 and in an equivalent of 200 g ai/10 a, respectively. 35 Days after the chemical treatment, the plant length and the number of tiller stems were measured. The determined values are shown in Table 5.

Comparative Examples 9 to 20

Rice was grown in the same manner as in each of Examples 27 to 38, except for not spraying a benzoic acid compound over the pot. The determined values are shown in Table 5.

TABLE 5

| | Herbicidal compound [test dose (g ai/10 a)] | Plant length (% ratio relative to that of untreated area) | Number of tiller stems |
|---|---|---|---|
| Example 27 | Bensulfuron-methyl | 83 | 7.2 |
| Comparative Example 9 | [15] | 75 | 5.2 |

TABLE 5-continued

| Herbicidal compound [test dose (g ai/10 a)] | | Plant length (% ratio relative to that of untreated area) | Number of tiller stems |
|---|---|---|---|
| Example 28 | pyrazosulfuron-ethyl | 92 | 8.0 |
| Comparative Example 10 | [6] | 85 | 7.8 |
| Example 29 | halosulfuron-methyl | 96 | 9.8 |
| Comparative Example 11 | [12] | 95 | 7.8 |
| Example 30 | Pyriftalid | 89 | 5.3 |
| Comparative Example 12 | [36] | 86 | 4.8 |
| Example 31 | Pyriminobac-methyl | 98 | 7.2 |
| Comparative Example 13 | [20] | 69 | 4.8 |
| Example 32 | Penoxsulam | 81 | 6.3 |
| Comparative Example 14 | [3.5] | 71 | 3.7 |
| Example 33 | Pretilachlor | 103 | 8.0 |
| Comparative Example 15 | [120] | 81 | 5.7 |
| Example 34 | Thiobencarb | 97 | 11.5 |
| Comparative Example 16 | [400] | 90 | 9.2 |
| Example 35 | Fentrazamide | 74 | 6.0 |
| Comparative Example 17 | [60] | 73 | 5.5 |
| Example 36 | AVH-301 | 62 | 3.2 |
| Comparative Example 18 | [60] | 23 | 1.0 |
| Example 37 | Chlomeprop | 107 | 7.7 |
| Comparative Example 19 | [90] | 104 | 5.5 |
| Example 38 | Oxaziclomefone | 87 | 10.8 |
| Comparative Example 20 | [12] | 86 | 8.5 |
| Untreated area | — | 100 | 11.8 |

As is clear from Table 4 and Table 5, phytotoxicity such as growth inhibition or tillering inhibition was more reduced in respective Examples in which a benzoic acid compound was sprayed than in Comparative Examples in which the compound was not sprayed. Thus, the pesticide composition of the present invention can be applied even to a paddy field in a bad environment such as a sandy soil or water-leaking paddy field.

Examples of various formulations of the composition of the present invention will be illustrated below.

Example 39

An appropriate volume of water was added to 1 part of the herbicidal compound A1, 5 parts of p-(n-propyl)benzoic acid, 3 parts of pregelatinized starch, 30 parts of calcium carbonate, and 61 parts of clay for kneading followed by extrusion granulation through a screen of 1 mm mesh opening diameter with an extrusion granulator, drying in a fluidized-bed dryer at a material temperature of 60° C., and screening to give granules containing the herbicidal compound A1 and p-(n-propyl)benzoic acid.

Example 40

An appropriate volume of water was added to 0.7 part of the herbicidal compound A1, 10 parts of p-(n-butyl)benzoic acid, 3 parts of enzyme-modified dextrin, 30 parts of calcium carbonate, and 56.3 parts of clay for kneading followed by extrusion granulation through a screen of 1 mm mesh opening diameter with an extrusion granulator, drying in a fluidized-bed dryer at a material temperature of 60° C., and screening to give granules containing the herbicidal compound A1 and p-(n-butyl)benzoic acid.

Example 41

An appropriate volume of water was added to 0.7 part of the herbicidal compound A1, 10 parts of p-(n-amyl)benzoic acid, 3 parts of pregelatinized starch, 1 part of dioctyl sodium sulfosuccinate, 30 parts of calcium carbonate, and 55.3 parts of clay for kneading followed by extrusion granulation through a screen of 1 mm mesh opening diameter with an extrusion granulator, drying in a fluidized-bed dryer at a material temperature of 60° C., and screening to give granules containing the herbicidal compound A1 and p-(n-amyl)benzoic acid.

Example 42

An appropriate volume of water was added to 1 part of the herbicidal compound A1, 5 parts of p-(n-hexyl)benzoic acid, 3 parts of enzyme-modified dextrin, 1 part of sodium dodecylbenzenesulfonate, and 90 parts of calcium carbonate for kneading followed by extrusion granulation through a screen of 1 mm mesh opening diameter with an extrusion granulator, drying in a fluidized-bed dryer at a material temperature of 60° C., and screening to give granules containing the herbicidal compound A1 and p-(n-hexyl)benzoic acid.

Example 43

An appropriate volume of water was added to 0.7 part of the herbicidal compound A1, 10 parts of p-(t-butyl)benzoic acid, 3 parts of pregelatinized starch, and 61 parts of calcium carbonate for kneading followed by extrusion granulation through a screen of 1 mm mesh opening diameter with an extrusion granulator, drying in a fluidized-bed dryer at a material temperature of 60° C., and screening to give granules containing the herbicidal compound A1 and p-(t-butyl)benzoic acid.

Example 44

An appropriate volume of water was added to 1 part of the herbicidal compound A1, 5 parts of sodium p-(t-butyl)benzoate, 3 parts of pregelatinized starch, 5 parts of distearyldimethylammonium chloride, 30 parts of clay, and 56 parts of calcium carbonate for kneading followed by extrusion granulation through a screen of 1 mm mesh opening diameter with an extrusion granulator, drying in a fluidized-bed dryer at a material temperature of 60° C., and screening to given granules containing the herbicidal compound A1 and sodium p-(t-butyl)benzoate.

Example 45

An appropriate volume of water was added to 2 parts of the herbicidal compound A1, 5 parts of n-butyl p-hydroxybenzoate, 3 parts of pregelatinized starch, 3 parts of dioctyl sodium sulfosuccinate, 20 parts of clay, and 67 parts of calcium carbonate for kneading followed by extrusion granulation through a screen of 1 mm mesh opening diameter with an extrusion granulator, drying in a fluidized-bed dryer at a material temperature of 60° C., and screening to give granules containing the herbicidal compound A1 and n-butyl p-hydroxybenzoate.

Example 46

20 Parts of the herbicidal compound A1, 30 parts of p-(t-butyl)benzoic acid, 5 parts of fumed silica (white carbon), 5 parts of sodium alkylnaphthalenesulfonate, and 40 parts of clay were mixed and pulverized with an impact mill to give a wettable powder containing the herbicidal compound A1 and p-(t-butyl)benzoic acid.

Example 47

2 Parts of the herbicidal compound A1, 10 parts of p-(t-butyl)benzoic acid, 5 parts of polyoxyethylene styryl phenyl ether sulfate sodium salt, 10 parts of propylene glycol, 0.3 part of xanthan gum, and 72.7 parts of water were mixed and pulverized with a wet-process grinder using glass beads as a grinding medium to give a flowable containing the herbicidal compound A1 and p-(t-butyl)benzoic acid.

Example 48

An appropriate volume of water was added to 5 parts of the herbicidal compound A1, 15 parts of sodium p-(t-butyl)benzoate, 3 parts of enzyme-modified dextrin, 3 parts of acetylene diol, 12 parts of hydrated hollow plastic beads, 20 parts of anhydrous sodium sulfate, and 42 parts of urea for kneading followed by extrusion granulation using an extrusion granulator through a screen of 5 mm mesh opening diameter and particle size assorting was conducted to have a length of 3 to 20 mm followed by drying in a fluidized-bed dryer at a material temperature of 60° C., and screening to give floating diffusion-type granules containing the herbicidal compound A1 and sodium p-(t-butyl)benzoate.

Example 49

An appropriate volume of water was added to 0.7 part of the herbicidal compound A1, 3 parts of pregelatinized starch, 7 parts of dioleyldimethylammonium chloride, 20 parts of clay, and 69.3 parts of calcium carbonate for kneading followed by extrusion granulation through a screen of 1 mm mesh opening diameter with an extrusion granulator, drying in a fluidized-bed dryer at a material temperature of 60° C., and screening to give granules containing the herbicidal compound A1. Separately, an appropriate volume of water was added to 10 parts of p-(t-butyl)benzoic acid, 3 parts of pregelatinized starch, 2 parts of sodium dodecylbenzenesulfonate, 20 parts of clay, and 65 parts of calcium carbonate for kneading followed by extrusion granulation through a screen of 1 mm mesh opening diameter with an extrusion granulator, drying in a fluidized-bed dryer at a material temperature of 60° C., and screening to give granules containing p-(t-butyl) benzoic acid. These granules were mixed and formulated to obtain mixed granules.

Example 50

An appropriate volume of water was added to 1 part of bensulfuron-methyl, 15 parts of p-(n-propyl)benzoic acid, 3 parts of enzyme-modified dextrin, 1 part of sodium dodecylbenzenesulfonate, 25 parts of bentonite, and 55 parts of calcium carbonate for kneading followed by extrusion granulation through a screen of 1 mm mesh opening diameter with an extrusion granulator, drying in a fluidized-bed dryer at a material temperature of 60° C., and screening to give granules containing bensulfuron-methyl and p-(n-propyl)benzoic acid.

Example 51

An appropriate volume of water was added to 2 parts of pyriftalid, 10 parts of p-(n-butyl)benzoic acid, 3 parts of enzyme-modified dextrin, 1 part of sodium dodecylbenzenesulfonate, 25 parts of bentonite, and 59 parts of calcium carbonate for kneading followed by extrusion granulation through a screen of 1 mm mesh opening diameter with an extrusion granulator, drying in a fluidized-bed dryer at a material temperature of 60° C., and screening to give granules containing pyriftalid and p-(n-butyl)benzoic acid.

Example 52

An appropriate volume of water was added to 1 part of pyriminobac-methyl, 10 parts of p-(n-amyl)benzoic acid, 3 parts of enzyme-modified dextrin, 1 part of sodium dodecylbenzenesulfonate, 25 parts of bentonite, and 60 parts of calcium carbonate for kneading followed by extrusion granulation through a screen of 1 mm mesh opening diameter with an extrusion granulator, drying in a fluidized-bed dryer at a material temperature of 60° C., and screening to give granules containing pyriminobac-methyl and p-(n-amyl)benzoic acid.

Example 53

An appropriate volume of water was added to 0.2 part of penoxsulam, 4 parts of p-(n-hexyl)benzoic acid, 3 parts of enzyme-modified dextrin, 1 part of sodium dodecylbenzenesulfonate, 25 parts of bentonite, and 66.8 parts of calcium carbonate for kneading followed by extrusion granulation through a screen of 1 mm mesh opening diameter with an extrusion granulator, drying in a fluidized-bed dryer at a material temperature of 60° C., and screening to give granules containing penoxsulam and p-(n-hexyl)benzoic acid.

Example 54

An appropriate volume of water was added to 10 parts of butachlor, 20 parts of p-(t-butyl)benzoic acid, 3 parts of enzyme-modified dextrin, 1 part of sodium dodecylbenzenesulfonate, 5 parts of fumed silica (white carbon), 5 parts of diatomaceous earth, 20 parts of bentonite, and 36 parts of calcium carbonate for kneading followed by extrusion granulation through a screen of 1 mm mesh opening diameter with an extrusion granulator, drying in a fluidized-bed dryer at a material temperature of 60° C., and screening to give granules containing butachlor and p-(t-butyl)benzoic acid.

Example 55

An appropriate volume of water was added to 16 parts of thiobencarb, 4 parts of sodium p-(t-butyl)benzoate, 3 parts of enzyme-modified dextrin, 1 part of sodium dodecylbenzenesulfonate, 5 parts of fumed silica (white carbon), 5 parts of diatomaceous earth, 20 parts of bentonite, and 46 parts of calcium carbonate for kneading followed by extrusion granulation through a screen of 1 mm mesh opening diameter with an extrusion granulator, drying in a fluidized-bed dryer at a material temperature of 60° C., and screening to give granules containing thiobencarb and sodium p-(t-butyl)benzoate.

Example 56

An appropriate volume of water was added to 3 parts of fentrazamide, 10 parts of (n-butyl) p-hydroxybenzoate, 3 parts of enzyme-modified dextrin, 1 part of sodium dodecylbenzenesulfonate, 25 parts of bentonite, and 58 parts of calcium carbonate for kneading followed by extrusion granulation through a screen of 1 mm mesh opening diameter with an extrusion granulator, drying in a fluidized-bed dryer at a material temperature of 60° C., and screening to give granules containing fentrazamide and (n-butyl) p-hydroxybenzoate.

Example 57

An appropriate volume of water was added to 1 part of oxaziclomefone, 20 parts of p-(n-butyl)benzoic acid, 3 parts of enzyme-modified dextrin, 1 part of sodium dodecylbenzenesulfonate, 25 parts of bentonite, and 50 parts of calcium carbonate for kneading followed by extrusion granulation through a screen of 1 mm mesh opening diameter with an extrusion granulator, drying in a fluidized-bed dryer at a material temperature of 60° C., and screening to give granules containing oxaziclomefone and p-(n-butyl)benzoic acid.

Example 58

An appropriate volume of water was added to 1 part of bensulfuron-methyl, 1 part of pyriminobac-methyl, 10 parts of p-(t-butyl)benzoic acid, 3 parts of enzyme-modified dextrin, 1 part of sodium dodecylbenzenesulfonate, 25 parts of bentonite, and 59 parts of calcium carbonate for kneading followed by extrusion granulation through a screen of 1 mm mesh opening diameter with an extrusion granulator, drying in a fluidized-bed dryer at a material temperature of 60° C., and screening to give granules containing bensulfuron-methyl, pyriminobac-methyl, and p-(t-butyl)benzoic acid.

Example 59

An appropriate volume of water was added to 1 part of bensulfuron-methyl, 2 parts of fentrazamide, 10 parts of p-(t-butyl)benzoic acid, 3 parts of enzyme-modified dextrin, 1 part of sodium dodecylbenzenesulfonate, 25 parts of bentonite, and 58 parts of calcium carbonate for kneading followed by extrusion granulation through a screen of 1 mm mesh opening diameter with an extrusion granulator, drying in a fluidized-bed dryer at a material temperature of 60° C., and screening to give granules containing bensulfuron-methyl, fentrazamide, and p-(t-butyl)benzoic acid.

Example 60

An appropriate volume of water was added to 6 parts of pyrazosulfuron-ethyl, 30 parts of p-(t-butyl)benzoic acid, 10 parts of sodium alkylnaphthalenesulfonate, 15 parts of diatomaceous earth, and 39 parts of clay for kneading followed by extrusion granulation through a screen of 0.6 mm mesh opening diameter with an extrusion granulator, drying in a fluidized-bed dryer at a material temperature of 60° C., and screening to give water dispersible granules containing pyrazosulfuron-ethyl and p-(t-butyl)benzoic acid.

Example 61

0.5 Part of halosulfuron-methyl, 50 parts of p-(t-butyl)benzoic acid, 5 parts of sodium alkylnaphthalenesulfonate, 5 parts of sodium lauryl sulfate, 10 parts of diatomaceous earth, and 29.5 parts of clay were mixed and pulverized with an impact mill to give a wettable powder containing halosulfuron-methyl and p-(t-butyl)benzoic acid.

Example 62

1 Part of bensulfuron-methyl, 1 part of pyriminobac-methyl, 20 parts of p-(t-butyl)benzoic acid, 15 parts of polyoxyethylene styryl phenyl ether sulfate sodium, 10 parts of propylene glycol, 0.2 part of xanthan gum, and 52.8 parts of water were mixed and pulverized with a wet-process grinder using glass beads as a grinding medium to give a flowable containing bensulfuron-methyl, pyriminobac-methyl, and p-(t-butyl)benzoic acid.

Example 63

An appropriate volume of water was added to 3 parts of bensulfuron-methyl, 1 part of pyriminobac-methyl, 50 parts of p-(t-butyl)benzoic acid, 2 parts of enzyme-modified dextrin, 3 parts of acetylene diol, 10 parts of hydrated hollow plastic beads, 15 parts of anhydrous sodium sulfate, and 16 parts of urea for kneading followed by extrusion granulation through a screen of 5 mm mesh opening diameter with an extrusion granulator and particle size assorting was conducted to have a length of 3 to 20 mm followed by drying in a fluidized-bed dryer at a material temperature of 60° C., and screening to give floating diffusion-type granules containing bensulfuron-methyl, pyriminobac-methyl, and p-(t-butyl) benzoic acid.

Next, examples of the phytotoxicity reduction method of the present invention will be illustrated below.

Example 64

An appropriate volume of water was added to 0.7 part of the herbicidal compound A1, 3 parts of pregelatinized starch, 20 parts of clay, and 76.3 parts of calcium carbonate for kneading followed by extrusion granulation through a screen of 1 mm mesh opening diameter with an extrusion granulator, drying in a fluidized-bed dryer at a material temperature of 60° C., and screening to give granules containing the herbicidal compound A1. Separately, 10 parts of p-(t-butyl)benzoic acid, 2 parts of sodium alkylnaphthalenesulfonate, 30 parts of diatomaceous earth, and 58 parts of clay were mixed and pulverized with an impact mill to give a wettable powder containing p-(t-butyl)benzoic acid. The granules and the wettable powder were simultaneously applied to paddy weeds.

Example 65

The granules containing the herbicidal compound A1 produced in the above-mentioned Example 64 were applied to paddy weeds. After three days, the wettable powder containing p-(t-butyl)benzoic acid produced in the above-mentioned Example 64 was applied to the paddy weeds.

Example 66

The wettable powder containing p-(t-butyl)benzoic acid produced in the above-mentioned Example 64 was applied to paddy weeds. After seven days, the granules containing the herbicidal compound A1 produced in the above-mentioned Example 64 were applied to the paddy weeds.

INDUSTRIAL APPLICABILITY

The pesticide composition of the present invention can exhibit a sufficient herbicidal effect and reduce or prevent phytotoxic symptoms, in the objective crop such as rice, including growth delay, growth inhibition, tillering inhibition, and etiolation, even though various herbicidal compounds used therein cause such phytotoxic symptoms in the objective crop when applied alone. Thus, the composition is useful as a herbicide for reducing or preventing phytotoxic symptoms in an objective crop or, in particular, as a herbicide that acts on rice or paddy rice.

Further, it is possible in the method of the present invention to reduce or prevent phytotoxic symptoms using a herbicidal ingredient in combination with a specific benzoic acid compound, even though the herbicidal ingredient is applied in an amount that allows an objective crop or, in particular, rice to exhibit phytotoxic symptoms such as growth retardation, growth inhibition, and etiolation. Thus, the method of the present invention is useful as a method for reducing phytotoxicity due to a herbicidal compound.

The invention claimed is:

1. A pesticide composition containing:
(A) a herbicidal compound in a herbicidally effective amount selected from the group consisting of sulfonylurea compounds, sulfonamide compounds, chloroacetanilide compounds, thiocarbamate compounds, pyrimidinyloxy(thio)benzoic acid compounds, tetrazolinone compounds, pyrazolate, pyrazoxyfen, benzofenap, cyclohexanedione compounds, phenoxycarboxylic acid compounds, oxazinone compounds, and difluoromethanesulfonylanilide compounds represented by the formula:

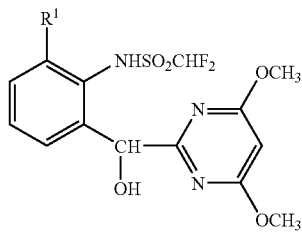

wherein $R^1$ is a hydrogen atom, an alkyl group, or an alkoxyalkyl group, or a salt thereof; and
(B) a compound selected from benzoic acid compounds represented by the formula:

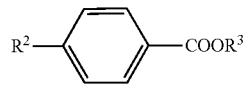

wherein $R^2$ is an alkyl group having 1 to 15 carbon atoms, and $R^3$ is a hydrogen atom or a metal atom,
wherein the benzoic acid compound is present in an amount effective to reduce the phytotoxicity of the herbicidal compound.

2. The pesticide composition according to claim 1, wherein the sulfonylurea compound is bensulfuron-methyl, pyrazosulfuron-ethyl, halosulfuron-methyl, azimsulfron, cinosulfuron, cyclosulfamuron, flucetosulfuron, imazosulfuron, or ethoxysulfuron.

3. The pesticide composition according to claim 1, wherein the sulfonamide compound is penoxsulam.

4. The pesticide composition according to claim 1, wherein the chloroacetanilide compound is butachlor, pretilachlor, or thenylchlor.

5. The pesticide composition according to claim 1, wherein the thiocarbamate compound is thiobencarb, esprocarb, or molinate.

6. The pesticide composition according to claim 1, wherein the pyrimidinyloxy(thio)benzoic acid compound is pyriminobac-methyl, pyriftalid, bispyribac-sodium, or pyribenzoxime.

7. The pesticide composition according to claim 1, wherein the tetrazolinone compound is fentrazamide.

8. The pesticide composition according to claim 1, wherein the cyclohexanedione compound is benzobicyclon, mesotrione, or a compound represented by the formula:

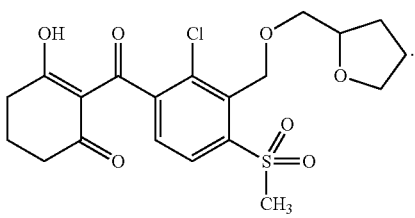

9. The pesticide composition according to claim 1, wherein the phenoxycarboxylic acid compound is 2,4-D, MCPA, MCPB, or chlomeprop.

10. The pesticide composition according to claim 1, wherein the oxazinone compound is oxaziclomefone.

11. The pesticide composition according to claim 1, which further comprises a surfactant.

12. The pesticide composition according to claim 1, wherein the herbicidal compound is selected from the group consisting of difluoromethanesulfonylanilide compounds.

13. The pesticide composition according to claim 1, wherein the difluoromethanesulfonylanilide compound is 2-[(4,6-dimethoxypyrimidin-2-yl)hydroxymethyl]-6-methoxymethyl-N-difluoromethanesulfonylanilide.

14. The pesticide composition according to claim 1, wherein $R^2$ is an alkyl group having 4 to 6 carbon atoms and $R^3$ is a hydrogen or sodium atom.

15. The pesticide composition according to claim 1, wherein the amount of the benzoic acid compound is 0.1 to 200 times relative to the amount of the herbicidal compound.

16. A method for reducing phytotoxicity by herbicidal compounds on crops which comprises applying, simultaneously or in close succession, to a crop, (A) a herbicidal compound in a herbicidally effective amount selected from the group consisting of sulfonylurea compounds, sulfonamide compounds, chloroacetanilide compounds, thiocarbamate compounds, pyrimidinyloxy(thio)benzoic acid compounds, tetrazolinone compounds, pyrazolate, pyrazoxyfen, benzofenap, cyclohexanedione compounds, phenoxycarboxylic acid compounds, oxazinone compounds, and difluoromethanesulfonylanilide compounds represented by the formula:

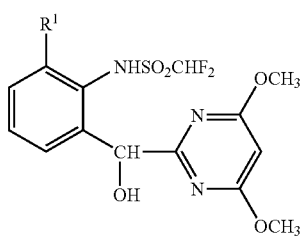

wherein $R^1$ is a hydrogen atom, an alkyl group, or an alkoxyalkyl group, or a salt thereof; and (B) a compound selected from benzoic acid compounds represented by the formula:

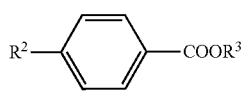

wherein $R^2$ is an alkyl group having 1 to 15 carbon atoms, and $R^3$ is a hydrogen atom or a metal atom,
wherein the benzoic acid compound is present in an amount effective to reduce the phytotoxicity of the herbicidal compound.

17. The method according to claim 16, wherein the amount of the benzoic acid compound is 0.1 to 200 times relative to the amount of the herbicidal compound.

18. The method according to claim 16, wherein the herbicidal compound is applied to the crop at a rate of 5 to 10,000 g/hectare.

* * * * *